(12) United States Patent
Musa

(10) Patent No.: US 6,803,406 B2
(45) Date of Patent: Oct. 12, 2004

(54) ELECTRON DONORS, ELECTRON ACCEPTORS AND ADHESION PROMOTERS CONTAINING DISULFIDE

(75) Inventor: Osama M. Musa, Hillsborough, NJ (US)

(73) Assignee: National Starch and Chemical Investmnet Holding Corporation, New Castle, DE (US)

( * ) Notice: Subject to any disclaimer, the term of this patent is extended or adjusted under 35 U.S.C. 154(b) by 80 days.

(21) Appl. No.: 10/113,059

(22) Filed: Mar. 29, 2002

(65) Prior Publication Data

US 2003/0191270 A1 Oct. 9, 2003

(51) Int. Cl.$^7$ .............................................. C08L 83/06
(52) U.S. Cl. ........................... 524/588; 528/27; 528/25; 526/310; 526/279; 568/61; 568/21; 556/482; 524/543
(58) Field of Search ...................... 528/27, 25; 526/310, 526/279, 346, 328.5; 568/61, 21; 556/482; 524/543, 588

(56) References Cited

U.S. PATENT DOCUMENTS

| | | | | |
|---|---|---|---|---|
| 3,278,484 | A | * | 10/1966 | Tesoro |
| 5,085,726 | A | * | 2/1992 | Omura et al. |
| 5,091,542 | A | | 2/1992 | Ahlem et al. |
| 5,440,358 | A | * | 8/1995 | Suzuki et al. |

FOREIGN PATENT DOCUMENTS

| | | |
|---|---|---|
| DE | 100 63 332 A1 | 6/2002 |
| EP | 0 572 077 A1 | 5/1993 |
| EP | 1 156 034 A1 | 11/2001 |
| EP | 1 156 053 | 11/2001 |
| JP | 62-084059 | 4/1987 |
| JP | 11-183701 | 7/1999 |
| JP | 2000-103940 | 4/2000 |
| SE | 224 515 | 8/1968 |

OTHER PUBLICATIONS

CAS Registry Search/12 Pages.

Choi, Jaesung, Yoon, Nung Min: "Synthesis of Disulfides by Copper–Catalyzed Disproportionation of Thiols"; Communications; J. Org. Chem. 1995, 60, 3266–3267; Feb. 22, 1995.

Walsh, Patrick J. et al.: "Asymmetric Dihydroxylation of Olefins Containing Sulfur: Chemoselective Oxidation of C–C Double Bonds in the Presence of Sulfides, 1,3–Dithianes, and Disulfides"; Tetrahedron Letters, vol. 35, No. 29, pp. 5129–5132, 1994; Great Britain; Elsevier Science Ltd.

Rabie, A. M.: "Synthesis and Characterization of Some Polyfunctional Thioalkylene Acrylate Monomers and Their Polymers—I"; European Polymer Journal, 1972, vol. 8, pp. 687–695, Pergamon Press, England.

Prabhu, Kandikere R. et al: "Reductive Dimerization of Organic Thiocyanates to Disulfides Mediated by Tetrathiomolybdate"; J. Org. Chem. 1995, 60, 7142–7143; Indian Institute of Science; Jun. 1, 1995.

Itoh, Shinobu et al.: "Fine Tuning of the Interaction between the Copper(1) and Disulfide Bond. Formation of a Bis($\mu$–thiolato)dicopper(II) Complex by Reductive Cleavage of the Disulfide Bond with Copper(I)"; J. Am. Chem. Soc. 2001, 123, 4087–4088; Web Apr. 7, 2001.

Lee, Yong–Kyung et al.: "Synthesis and Characterization of Novel Polymers Containing Sulfur from 3–Mercaptopropionic Acid"; Polymer Journal, vol. 32, No. 5. Pp 395–401 (2000).

* cited by examiner

Primary Examiner—Kuo-Liang Peng
(74) Attorney, Agent, or Firm—Jane E. Gennaro

(57) ABSTRACT

Disclosed are compounds comprising both disulfide functionality and electron donor functionality or alkoxy siloxane functionality, and curable compositions comprising compounds comprising both disulfide functionality and electron donor functionality, or electron acceptor functionality, or alkoxy siloxane functionality.

10 Claims, No Drawings

ELECTRON DONORS, ELECTRON ACCEPTORS AND ADHESION PROMOTERS CONTAINING DISULFIDE

FIELD OF THE INVENTION

This invention relates to compounds containing electron donor electron acceptor, or adhesion promoting functionality, and a disulfide functionality.

BACKGROUND OF THE INVENTION

Curable compositions are used in the fabrication and assembly of semiconductor packages and microelectronic devices, such as in bonding integrated circuit chips to substrates, bonding circuit assemblies to printed wire boards, coating lead frames, underfilling the gap between chip and substrate, and encapsulating the chip and substrate assembly.

Substrates used in the fabrication of semiconductor packages can be metal, ceramic, or laminate. There are a number of electron donor/electron acceptor systems that are used in the industry, but curable compositions that in general have good performance may be deficient when used on one or more of these substrates. The addition of adhesion promoters or the use of curable resins that contain adhesion promoting capability would serve to correct this deficiency.

SUMMARY OF THE INVENTION

This invention is a compound comprising both disulfide functionality and electron donor functionality or alkoxy siloxane functionality. In a further embodiment this invention is a curable composition comprising a compound comprising both disulfide functionality and electron donor functionality, or electron acceptor functionality, or alkoxy siloxane functionality.

DETAILED DESCRIPTION OF THE INVENTION

The compound containing electron donor or electron acceptor functionality and disulfide will have the structure:

$$(E)_m—Z—X—R—S—S—R'—X'—Z'—(E')_n$$

in which m and n are an integers of 0 to 500, provided that m and n cannot both be 0; E and E' are an electron donor or an electron acceptor; R and R' are a direct bond, a linear or branched alkyl or alkenyl group, or a cyclic alkyl or alkenyl group, or an aromatic group; Z and Z' are any organic moiety (polymeric, oligomeric, or monomeric); and X and X' are a direct bond, an alkyl group, or a functionality selected from the group consisting of.

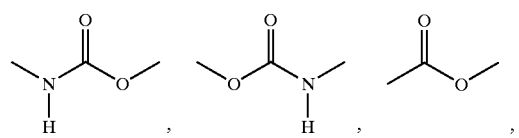

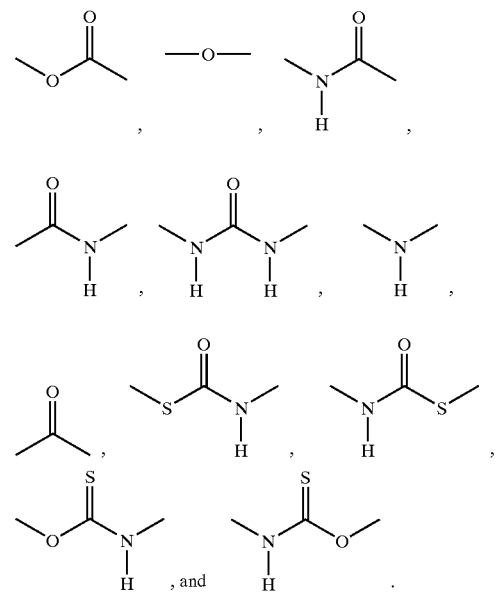

Exemplary electron donor groups include vinyl ether, vinyl silane, carbon to carbon double bonds attached to an aromatic ring and conjugated with the unsaturation in the aromatic ring, such as cinnamyl and styrenic groups. Exemplary electron acceptor groups are fumarates, maleates, maleimides and acrylates.

Exemplary Z groups include linear, branched or cyclic alkyl or alkenyl groups; aromatic groups, polyaromatic groups, heteroaromatic groups, siloxanes, polysiloxanes, polyethers, polyesters, polyurethanes, polysiloxanes, polycarbonates, polyacrylates, and poly(butadienes).

These compounds can be prepared by standard addition, condensation, and coupling reactions. As a first reaction example, a polymeric, oligomeric, or monomeric starting material containing both disulfide functionality and a reactive functionality can be reacted with a second starting material containing both electron donor or electron acceptor functionality and a complementary reactive functionality.

As a second reaction example, a starting material containing electron donor or electron acceptor functionality, disulfide functionality, and a reactive functionality can be reacted with a second starting material containing electron donor or electron acceptor functionality, disulfide functionality, and a complementary reactive functionality. Examples of reactive functionalities include hydroxyl and amino groups to be reacted with carboxyl and isocyanate groups.

As a third reaction example, two mercaptans containing electron donor or electron acceptor functionality can be reacted in a coupling reaction.

The compound containing alkoxy siloxane functionality and disulfide will have the structure:

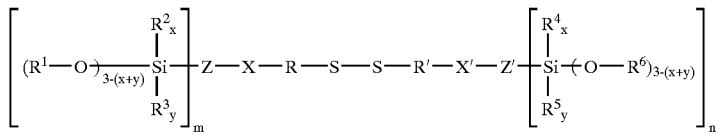

in which m and n are 0 to 500, provided both m and n are not 0; $R^1$ and $R^6$ are a methyl or ethyl group; $R^2$, $R^3$, $R^4$, and $R^5$ are a vinyl group, an aromatic group, or a linear or branched alkyl group, preferably of 1 to 4 carbons; R and R', X and X', and Z and Z' are as described above; x and y are 0 or 1.

These compounds are prepared in similar reactions to those described above, except that the polymeric, oligomeric, or monomeric starting materials will contain siloxane functionality in place of the electron donor or electron acceptor functionality.

Suitable starting materials for making electron donors and electron acceptors include, but are not limited to, hydroxybutyl vinyl ether, cinnamyl alcohol, isoeugenol, 1,4-cyclohexane-dimethanol monovinyl ether, hydroxyoctyl maleate, aminobutyl fumarate, N-(6-hydroxyhexyl) maleimide and 3-isopropenyl-α,α-dimethylbenzyl isocyanate.

With this understanding, those skilled in the art will be able to devise reaction schemes for making a myriad of materials falling within the above generic formula.

In another embodiment, this invention is a curable composition, such as an adhesive, coating, or encapsulant, containing the inventive compounds. The composition can be in paste form prepared by milling or blending the components, or in film form, made by film making techniques known to those skilled in the art. The curable composition will include optionally a curing agent, and optionally a filler.

In another embodiment, this invention is a curable composition containing the inventive compounds blended with one or more other curable resins. Preferred other curable resins include vinyl ethers, vinyl silanes, compounds or resins containing vinyl or allyl functionality, thiol-enes (a thiol-ene within this specification and claims is a compound or resin that is the reaction product of a thiol and a compound having carbon to carbon unsaturation), compounds or resins containing cinnamyl or styrenic functionality, fumarates, maleates, acrylates, maleimides, epoxies and cyanate esters.

Other curable resins that can be blended with the inventive compounds include hybrid compounds or resins that contain both epoxy and cinnamyl or styrenic or vinyl ether functionality; hybrid compounds or resins that contain both vinyl silane and cinnamyl or styrenic functionality, and hybrid compounds or resins that contain both vinyl silane and epoxy functionality.

Within the structures in this specification and claims, $C_{36}$ represents a mixture of isomers of linear and branched alkyl chains having 36 carbon atoms that are derived from linoleic and oleic acids.

Suitable other curable compounds or resins having vinyl ether or allyl functionality for blending with the inventive compounds include:

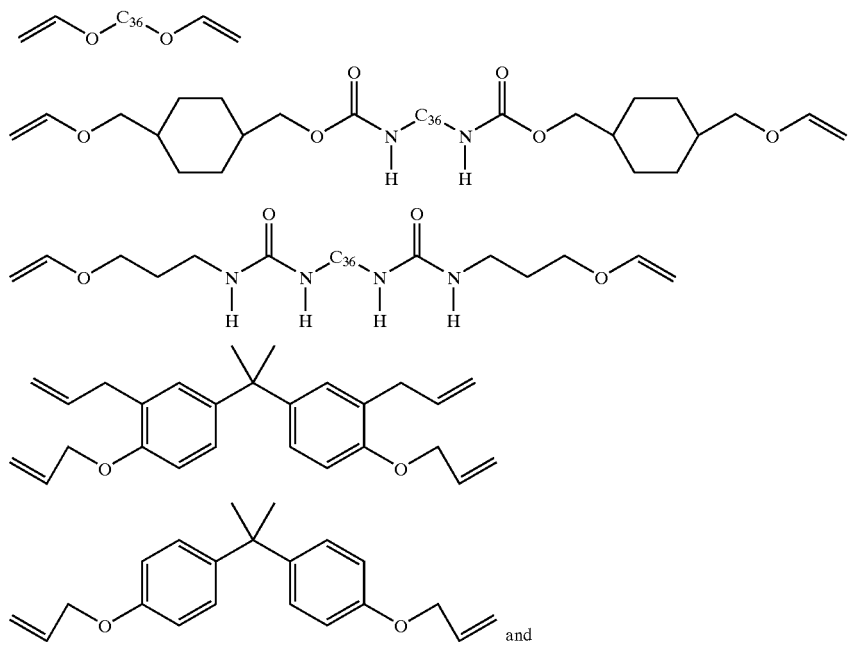

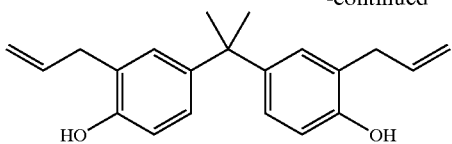

These compounds can be prepared by synthetic routes and from starting materials known to those skilled in the art. Other compounds containing vinyl or allyl functionality are commercially available from BASF, ISP, or Aldrich.

Suitable other curable compounds or resins for blending with the inventive compounds and containing both styrenic or cinnamyl and vinyl ether functionality are disclosed in U.S. Pat. No. 6,307,001 and include:

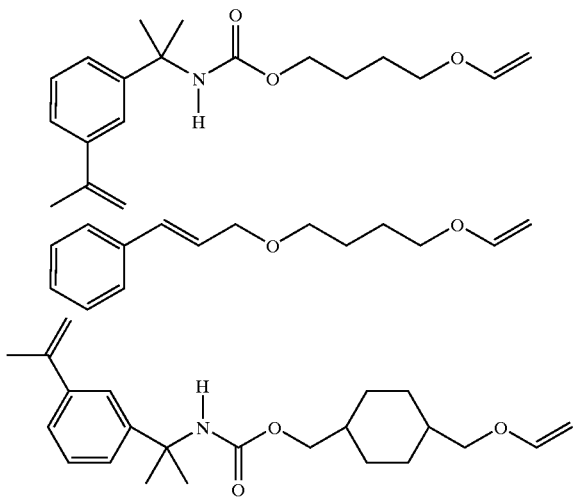

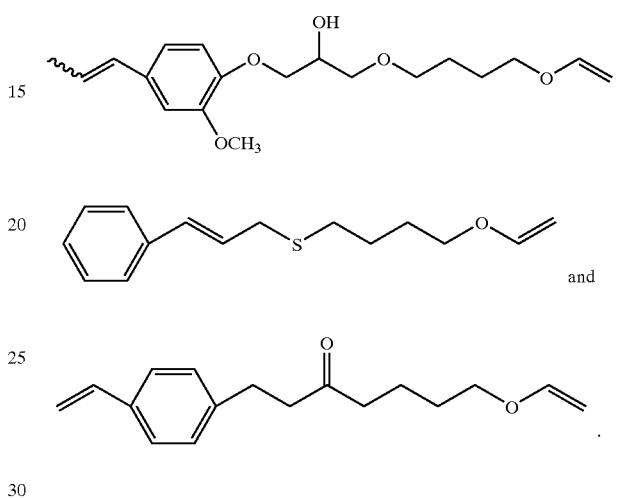

and

These compounds can be prepared by synthetic routes and from starting materials known to those skilled in the art, or by the routes disclosed in the identified patent.

Suitable other curable compounds for blending with the inventive compounds and containing styrenic or cinnamyl functionality include:

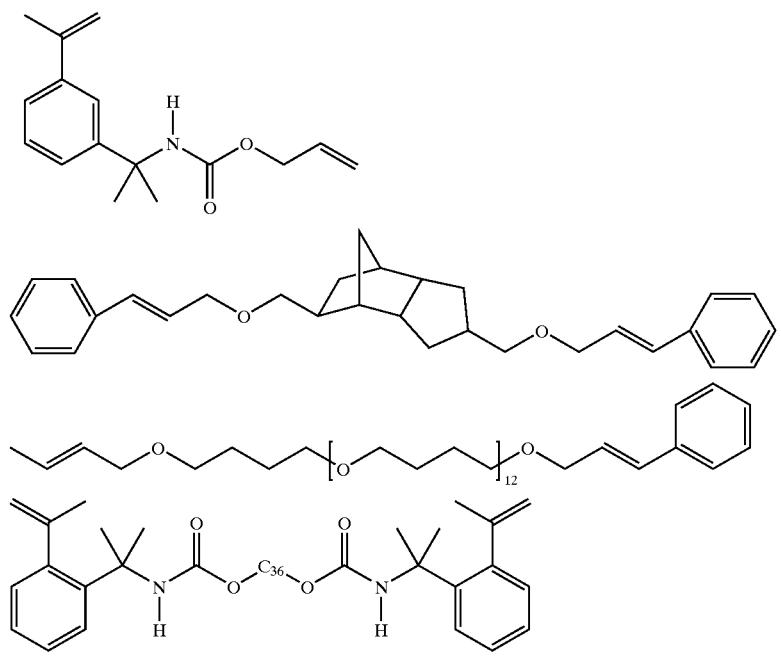

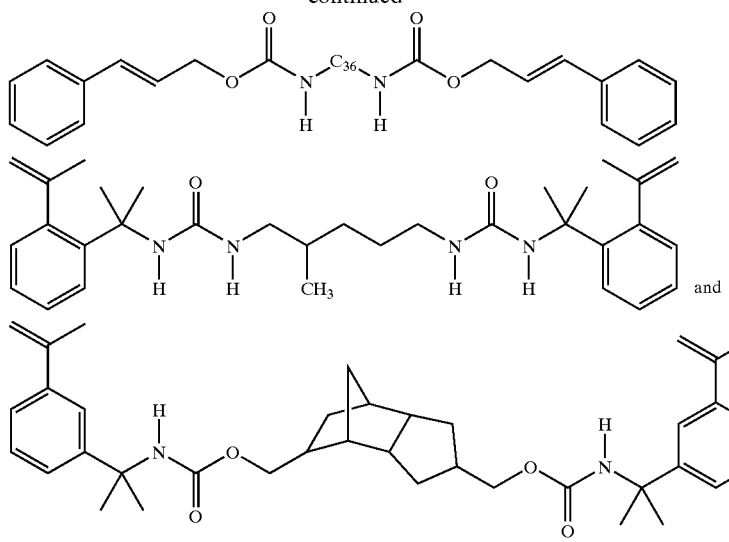

These compounds can be prepared by synthetic routes and from starting materials known to those skilled in the art.

Suitable other curable compounds for blending with the inventive compounds and containing alkoxy silane functionality and electron donor or electron acceptor functionality include:

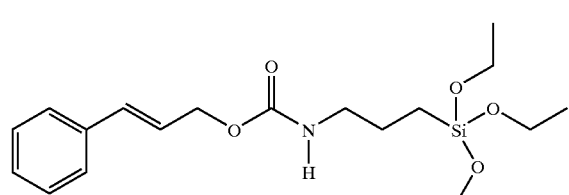

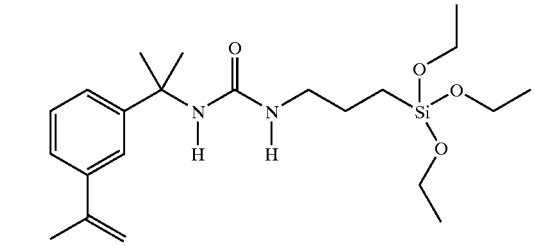

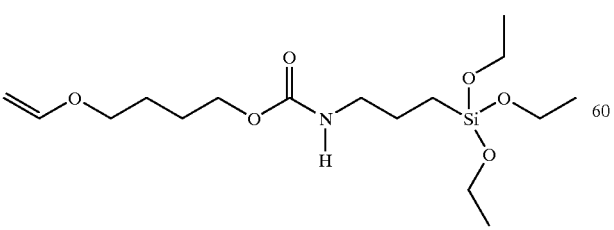

and

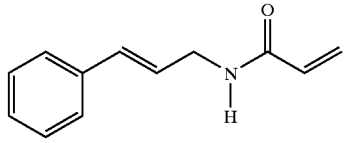

-continued

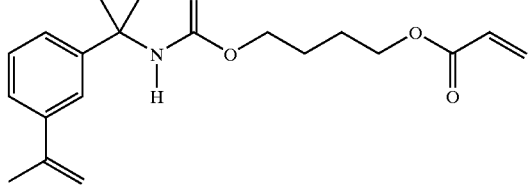

Suitable other curable compounds or resins for blending with the inventive compounds and containing styrenic or cinnamyl functionality with acrylate, maleate, fumarate or maleimide functionality, are disclosed in U.S. Pat. No. 6,300,456, and include:

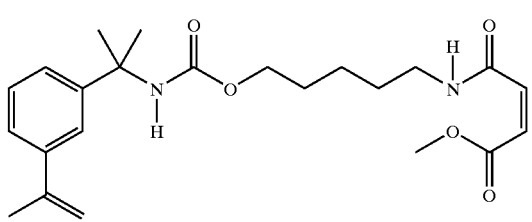

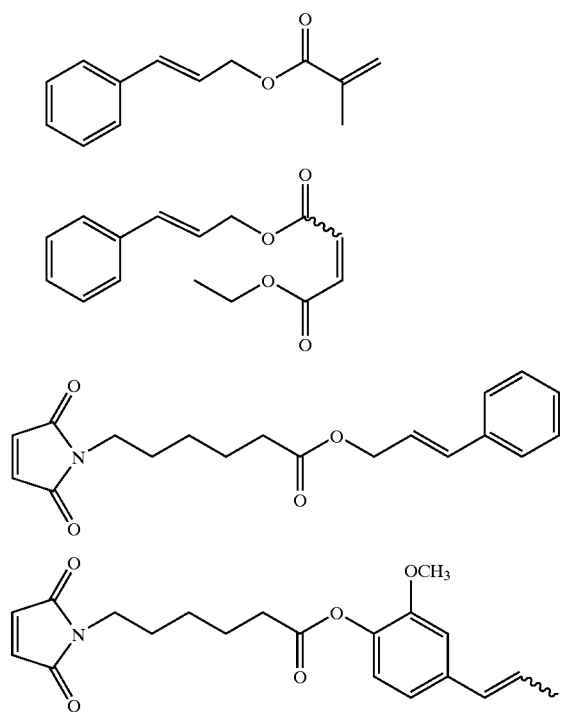
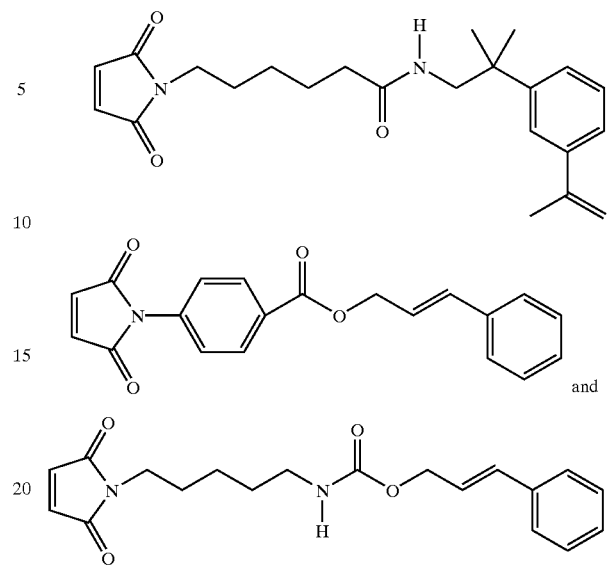
These compounds can be prepared by synthetic routes and from starting materials known to those skilled in the art, or by the routes disclosed in U.S. Pat. No. 6,300,456.
Additional curable maleimides for blending with the inventive compounds are those disclosed in U.S. Pat. Nos. 6,057,381, 6,063,828, 6,180,187, 6,187,886, 6,281,314, and 6,265,530, and include:
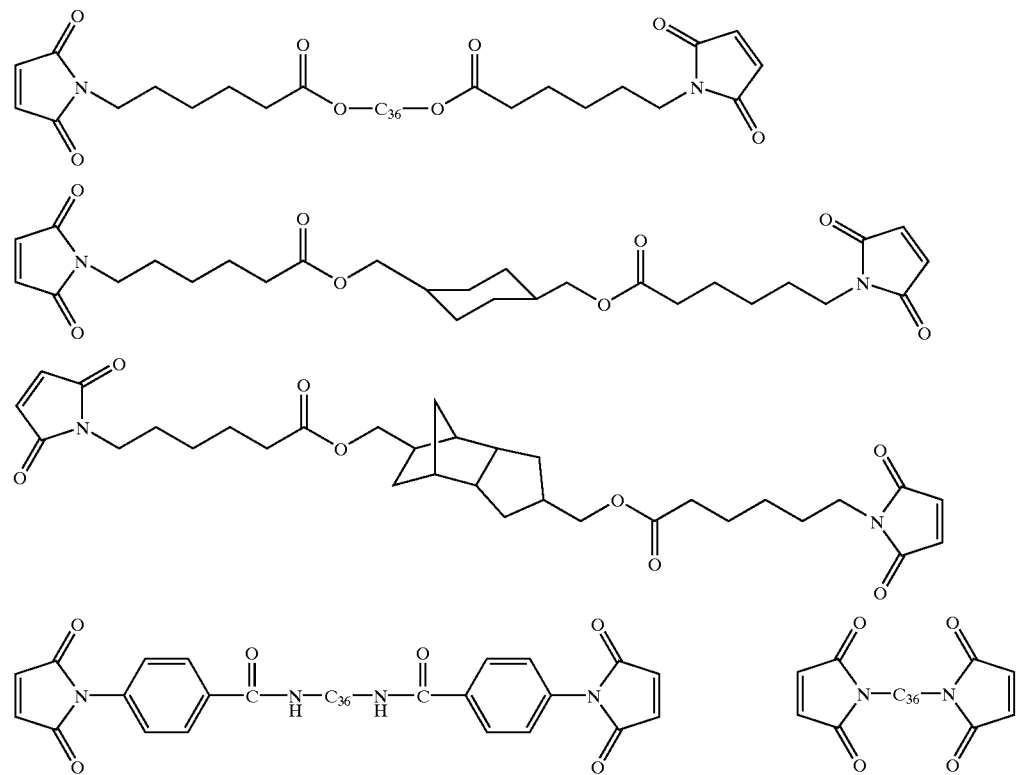

-continued

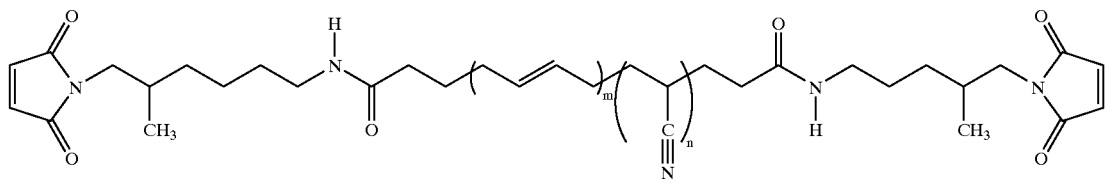

which resin is derived from a poly(butadiene) and in which m and n will vary depending on the particular poly (butadiene) starting material, (in one embodiment m and n will be integers to provide a number average molecular weight of 3600):

Additional curable maleates and fumarates for blending with the inventive compounds are dioctyl maleate, dibutyl maleate, dioctyl fumarate, dibutyl fumarate. Additional maleate and fumarates are available from Aldrich.

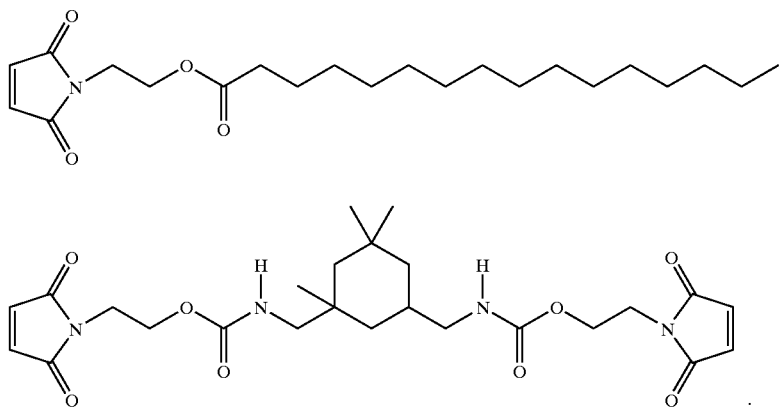

These compounds can be prepared by synthetic routes and from starting materials known to those skilled in the art, or by the routes disclosed in U.S. Pat. Nos. 6,057,381, 6,063,828, 6,180,187, 6,187,886, 6,281,314, and 6,265,530.

Additional other curable resins, which contain both epoxy and electron acceptor or electron donor functionality, for blending with the inventive compounds include the following:

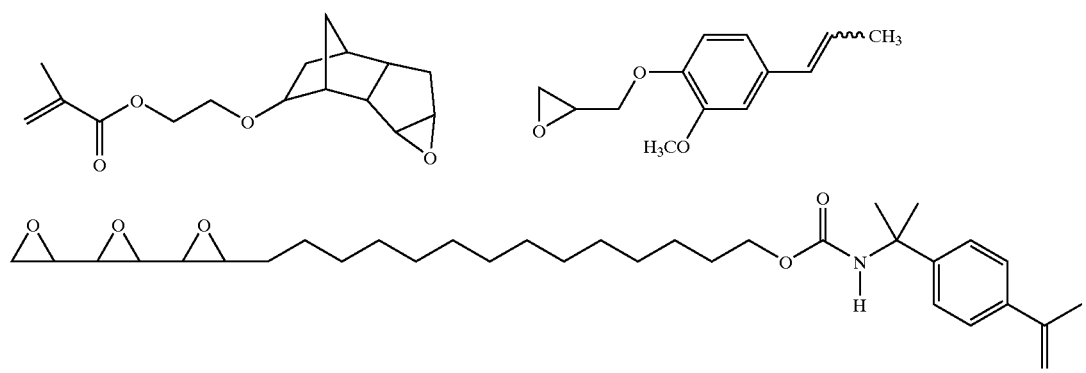

and

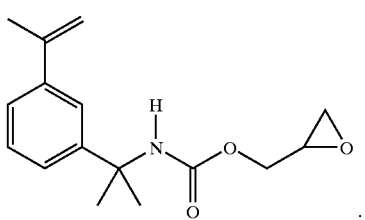
These compounds can be prepared by synthetic routes and from starting materials known to those skilled in the art.
Suitable curable compounds or resins containing both vinyl silane and electron donor or electron acceptor functionality for blending with the inventive compounds include:
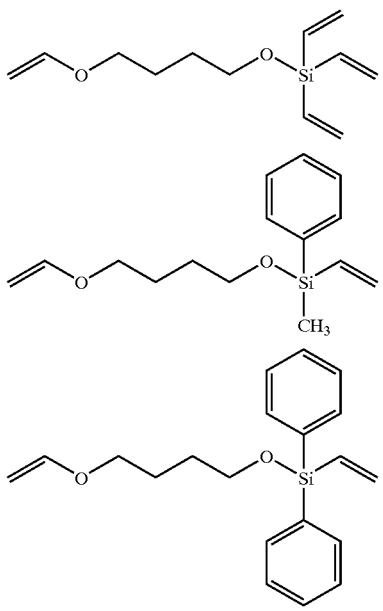
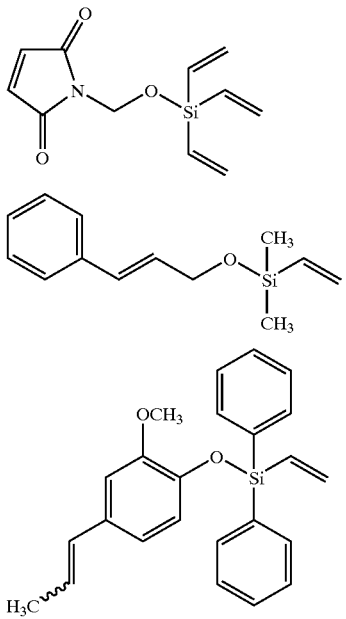
-continued
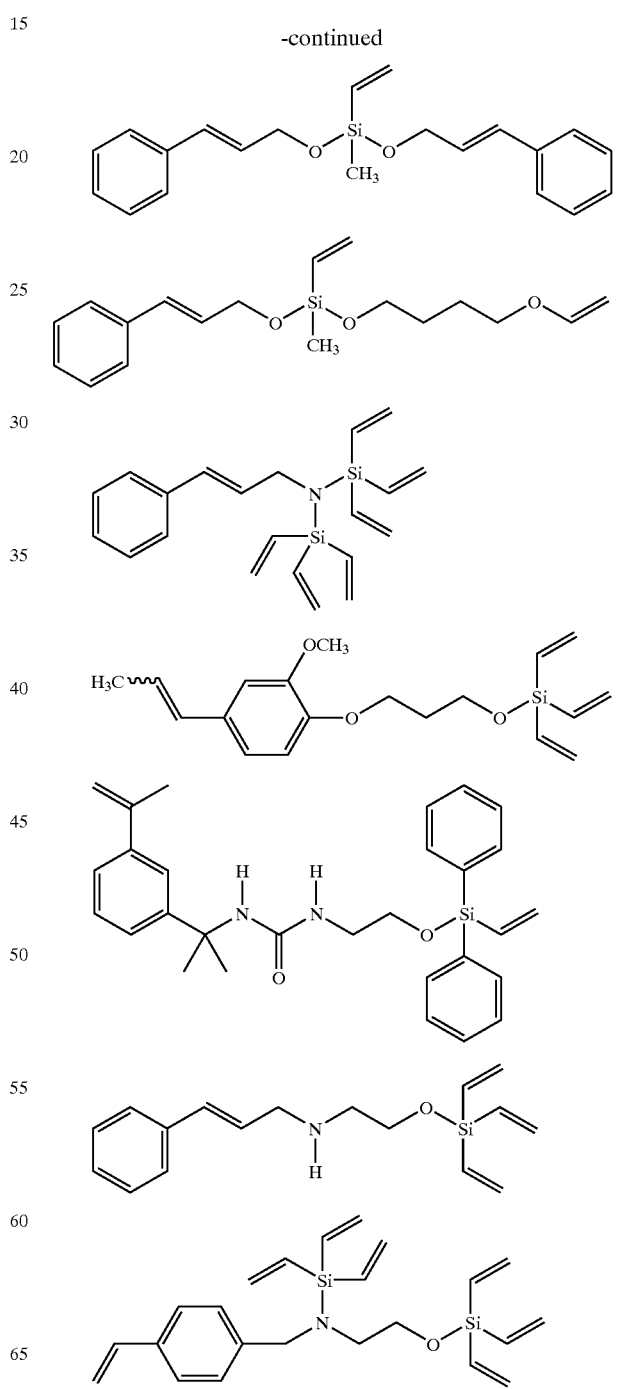

-continued

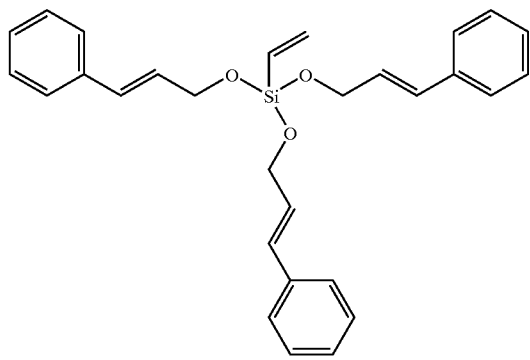

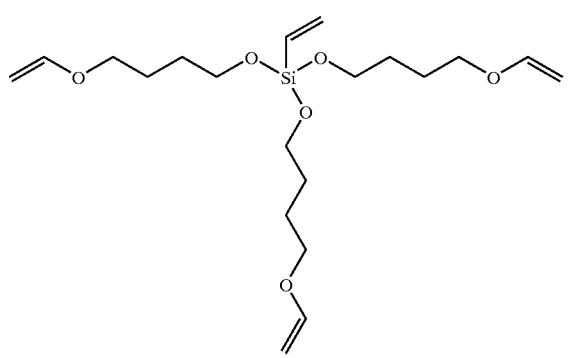

These compounds can be prepared by synthetic routes and from starting materials known to those skilled in the art.

Suitable other curable compounds or resins containing both vinyl silane and epoxy functionality for blending with the inventive compounds include (in which t-Bu means a tertiary butyl group):

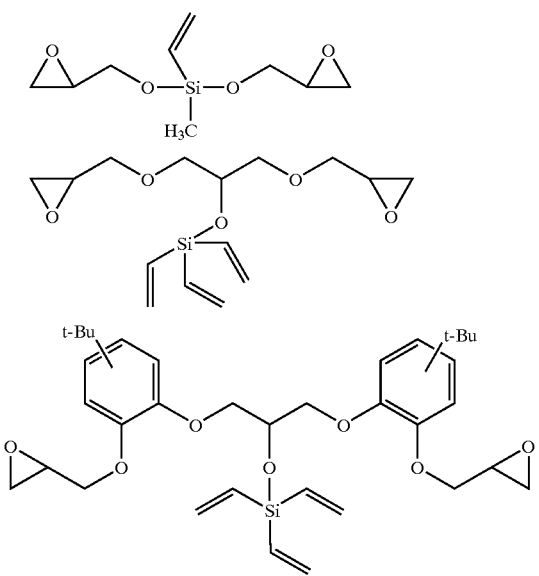

-continued

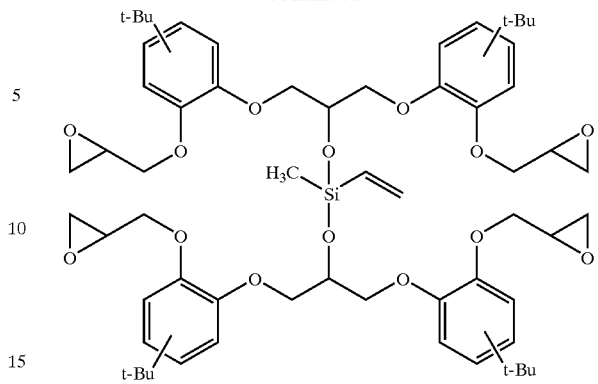

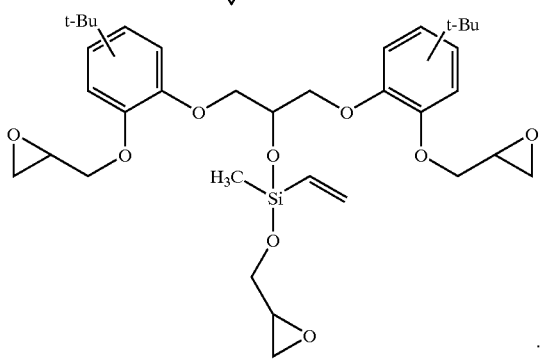

Suitable curable cyanate ester compounds or resins for blending with the inventive compounds are those containing one or more cyanate ester functional groups, —OCN, and are commercially available from Ciby Geigy or Dow Chemical. Examples include 1,1'-bis(4-cyanatophenyl)-ethane, bis(4-cyanate-3,5-dimethylphenyl)methane, 1,3-bis(cyanatophenyl-1-(1-methyl-ethylethyl-ethylidene)), 2,2'-bis(4-cyanatophenyl)isopropylidene Suitable thiol-enes, for example, are those disclosed in U.S. Pat. Nos. 3,653,959, 4,422,914, 4,442,198, 4,443,495, 4,451,636, 4,481,281.

If desired, curing agents can be added, such as, thermal initiators and photoinitiators present in an effective amount to cure the composition. In general, those amounts will range from 0.5% to 30%, preferably 1% to 20%, by weight of the total organic material (that is, excluding any inorganic fillers) in the composition. In general, the curable compositions will cure within a temperature range of 100° C. to 300° C., and curing will be effected within a range of ten seconds to three hours. The actual cure profile will vary with the components and can be determined without undue experimentation by the practitioner.

The curable compositions may also comprise nonconductive or thermally or electrically conductive fillers. Suitable nonconductive fillers are particles of vermiculite, mica, wollastonite, calcium carbonate, titania, sand, glass, fused silica, fumed silica, barium sulfate, and halogenated ethylene polymers, such as tetrafluoroethylene, trifluoroethylene, vinylidene fluoride, vinyl fluoride, vinylidene chloride, and vinyl chloride. Suitable conductive fillers are carbon black, graphite, gold, silver, copper, platinum, palladium, nickel, aluminum, silicon carbide, diamond, and alumina. If present, fillers generally will be in amounts of 20% to 90% by weight of the formulation.

EXAMPLES

Example 1

Resin A.

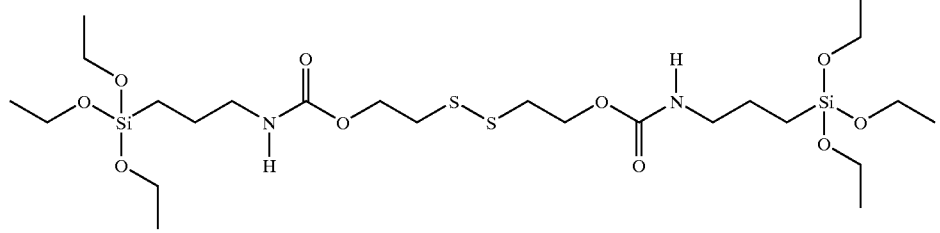

Silquest A-1310 (64.1 g, 0.26 mole, available from Witco) and 2-hydroxyethyl disulfide (20.0 g, 0.13 mole) were solvated in toluene (50 g) in a 500 mL three-necked flask equipped with a mechanical stirrer, condenser and nitrogen inlet/outlet. The reaction was placed under nitrogen, and dibutyltin dilaurate (0.07 g, 0.00011 mole) was added with stirring as the solution was heated to 80° C. The resulting mixture was heated for an additional three hours at 80° C. After the reaction was allowed to cool to room temperature, the solvent was removed in vacuo to give the product in 96% yield.

Example 2

Resin B.

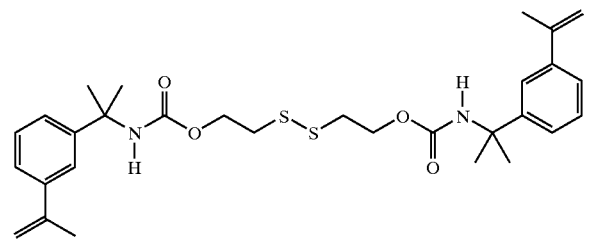

Meta unsaturated aliphatic isocyanate (m-TMI) (26.8 g, 0.133 mole, available from Cytec) and 2-hydroxyethyl disulfide (10.0 g, 0.066 mole) were solvated in toluene code (50 g) in a 250 mL three-necked flask equipped with a mechanical stirrer, condenser and nitrogen inlet/outlet. The reaction was placed under nitrogen, and dibutyltin dilaurate (0.07 g, 0.00011 mole) was added with stirring as the solution was heated to 80° C. The resulting mixture was heated for an additional six hours at 80° C. After the reaction was allowed to cool to room temperature, the solvent was removed in vacuo to give the product in 97% yield.

Example 3

The performance of the resin containing both electron donor (styrenic) and disulfide functionality, Resin B, from Example 2 was compared for die shear strength with a similar resin without disulfide functionality, designated Resin C, having the following structure:

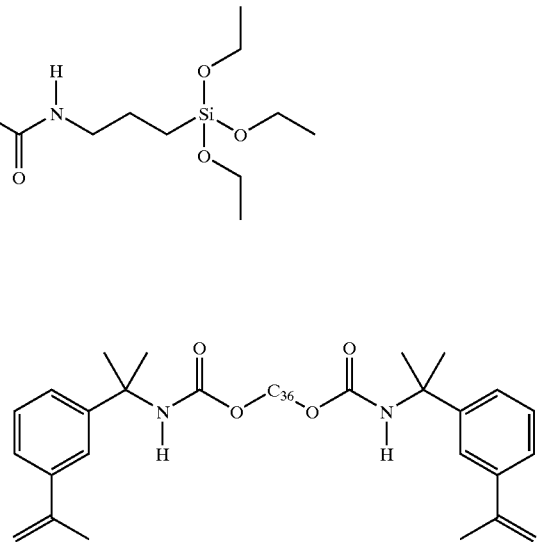

Each of the above resins was formulated into a die attach adhesive further comprising a bismaleimide, a rubber, a commercial adhesion promoter (Silquest A-174 from Witco), and 75% by weight silver flake.

Each adhesive was dispensed onto a copper leadframe and onto a silver coated leadframe. A silicon die (120×120 mil) was placed onto the adhesive, and the adhesive was cured on a hot plate at 200° C. for 60 seconds. Ten assemblies for each adhesive were prepared. Each die was sheared from the leadframe at 90 degrees with a Dage 2400-PC Die Shear Tester at 240° C. The results were pooled and averaged and are reported as Kilogram force in Table 1. The data show that the addition of a disulfide containing compound to the adhesive composition improves adhesive strength.

TABLE 1

| | Die Shear Strength in KgF @ 240° C. | |
|---|---|---|
| Adhesive with | Ag leadframe | Cu leadframe |
| Resin B | 1.6 | 1.8 |
| Resin C Control | 0.8 | 1.1 |

Example 4

The performance of the adhesion promoter containing disulfide functionality from Example 1, Resin A, was compared for die shear strength with a similar adhesion promoter without disulfide functionality (commercially available Silquest A-174 from Witco).

Each of the above adhesion promoters was formulated into a die attach adhesive further comprising a bismaleimide, a rubber, and resin C, and 75% by weight silver flake.

Each adhesive was dispensed onto a copper leadframe and onto a silver coated leadframe. A silicon die (120×120 mil) was placed onto the adhesive, and the adhesive was cured on a hot plate at 200° C. for 60 seconds. Ten assemblies for each adhesive were prepared. Each die was sheared from the leadframe at 90 degrees with a Dage 2400-PC Die Shear Tester at 240° C. The results were pooled and averaged and are reported as Kilogram force in Table 2. The data show that the addition of a disulfide containing compound to the adhesive composition improves adhesive strength.

TABLE 2

| | Die Shear Strength in KgF @ 240° C. | |
|---|---|---|
| Adhesive with | Ag leadframe | Cu leadframe |
| Resin A | 1.1 | 1.9 |
| Silquest A-174 Control | 0.5 | 1.3 |

What is claimed:

1. A compound having the structure $(E)_m$—Z—X—R—S—S—R'—X'—Z'—$(E')_n$ in which m and n are integers of 0 to 500, provided that m and n cannot both be 0;

E and E' are an electron donor selected from the group consisting of vinyl ether, vinyl silane, and cinnamyl;

R and R' are a direct bond, a linear or branched alkylene or alkenylene group, or a cyclic alkylene or alkenylene group, or an aromatic group;

Z and Z' are any organic moiety; and

X and X' are a direct bond, an alkylene group, or a functionality selected from the group consisting of:

2. The compound according to claim 1 in which Z and Z' are selected from the group consisting of linear, branched or cyclic alkylene or alkenylene groups; aromatic groups, polyaromatic groups, heteroaromatic groups, siloxanes, polysiloxanes, polyethers, polyesters, polyurethanes, polysiloxanes, polycarbonates, polyacrylates, and poly(butadienes).

3. The compound according to claim 1 in which X and X' are

4. A composition comprising a compound having the structure $(E)_m$—Z—X—R—S—S—R'—X'—Z'—$(E')_n$ in which m and n are an integer of 0 to 500, provided that m and n cannot both be 0;

E and E' are an electron donor or an electron acceptor group selected from the group consisting of vinyl ether, vinyl silane, cinnamyl, malemide, fumarate and maleate groups;

R and R' are a direct bond, a linear or branched alkylene or alkenylene group, or a cyclic alkylene or alkenylene group, or an aromatic group;

Z and Z' are any organic moiety; and

X and X' are a direct bond, an alkeylene group, or a functionality selected from the group consisting of:

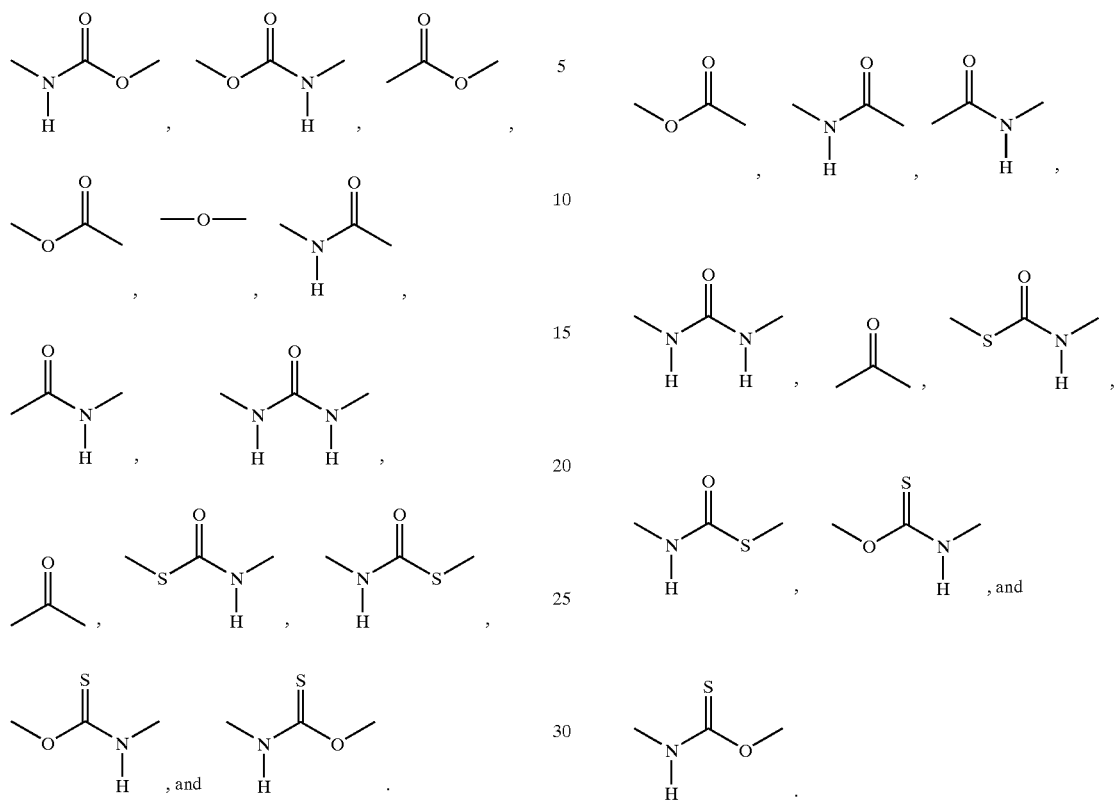

the composition further comprising optionally a curing agent and optionally a filler.

5. A compound having the structure

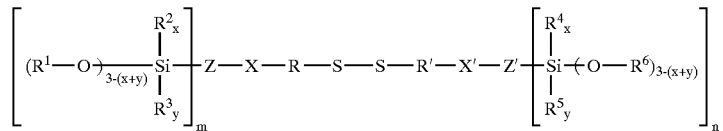

in which m and n are 0 to 500, provided both m and n are not 0;
$R^1$ and $R^5$ are a methyl or ethyl group;
$R^2$, $R^3$, $R^4$, and $R^5$ are a vinyl group, an aromatic group, or a linear or branched alkyl group;
x and y are 0 or 1;
Z and Z' are any organic moiety; and
X and X' are a functionality selected from the group consisting of 6. The compound according to claim 5 in which Z and Z' are selected from the group consisting of linear, branched or cyclic alkylene or alkenylene groups; aromatic groups, polyaromatic groups, heteroaromatic groups, siloxanes, polysiloxanes, polyethers, polyesters, polyurethanes, polysiloxanes, polycarbonates, polyacrylates, and poly (butadienes).

7. The compound according to claim 5 in which X and X' are

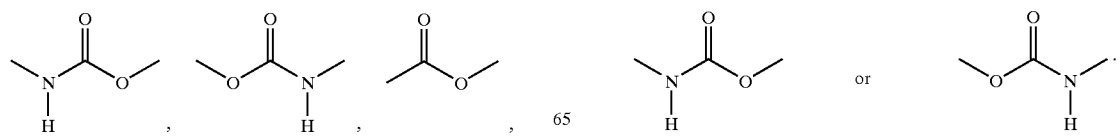

8. The compound according to claim 5 having the structure

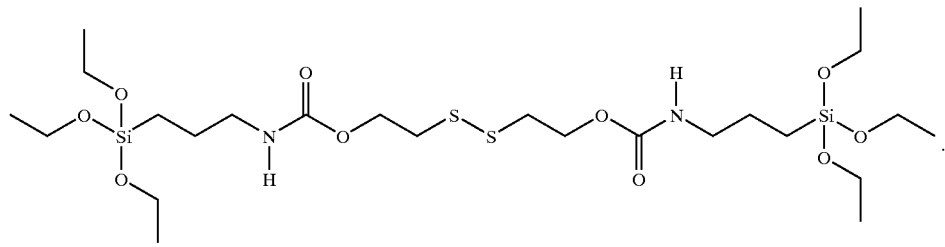

9. A composition comprising a compound having the structure

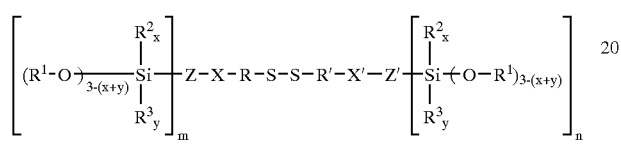

in which

R and R' are a direct bond, a linear or branched alkylene or alkenylene group, or a cyclic alkylene or alkenylene group, or an aromatic group;

m and n are 0 to 500, provided both m and n are not 0;

$R^1$ and $R^6$ are a methyl or ethyl group;

$R^2$, $R^3$, $R^4$, and $R^5$ are a vinyl group, an aromatic group, or a linear or branched alkyl group;

x and y are 0 or 1;

Z and Z' are any organic moiety; and

X and X' are a functionality selected from the group consisting of

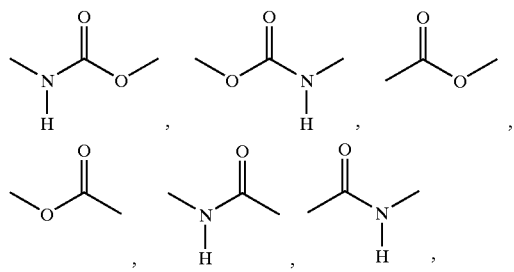

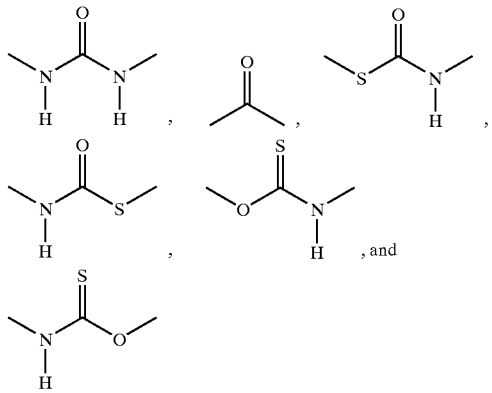

the composition further comprising optionally a curing agent and optionally a filler.

10. A composition according to claim 4 or 9, and one or more other curable compounds or resins selected from the group consisting of vinyl ethers, vinyl silanes, compounds or resins containing vinyl or allyl functionality, thiol-enes, compounds or resins containing cinnamyl or styrenic functionality, fumarates, maleates, acrylates, maleimides, epoxies, cyanate esters, compounds or resins that contain both epoxy and cinnamyl or styrenic or vinyl ether functionality; compounds or resins that contain both vinyl silane and cinnamyl or styrenic functionality, and compounds or resins that contain both vinyl silane and epoxy functionality.

* * * * *